United States Patent [19]

Dudley et al.

[11] Patent Number: 5,444,069

[45] Date of Patent: Aug. 22, 1995

[54] IMIDAZO-PYRIDINE ANGIOTENSIN II ANTAGONISTS USED TO TREAT MEMORY LOSS

[75] Inventors: David T. Dudley; John C. Hodges; Thomas A. Pugsley; Michael D. Taylor, all of Ann Arbor, Mich.

[73] Assignee: Warner-Lambert Company, Morris Plains, N.J.

[21] Appl. No.: 227,223

[22] Filed: Apr. 13, 1994

[51] Int. Cl.$^6$ ............... A61K 31/415; A61K 31/34
[52] U.S. Cl. .................... 514/303; 514/395; 514/397; 514/401; 514/402; 514/406; 514/468; 546/118
[58] Field of Search ............ 514/303, 397, 401, 402, 514/396, 468, 406; 546/118

[56] References Cited

U.S. PATENT DOCUMENTS 4,812,462  3/1989  Blankley et al. ............... 514/303

OTHER PUBLICATIONS

*Molecular Pharmacology,* vol. 37, No. 3, Mar. 1990, R. S. L. Chang et al., pp. 347–351.
*Peptide Research,* vol. 2, No. 3, May/Jun 1989, R. C. Speth et al., pp. 232–239.
*Research Topics in Physiology,* vol. 10, 1988, R. C. Speth et al., pp. 1–34.
Bumpus et al., *Hypertension,* 1991, 17, 720–721, "Nomenclature for Angiotensin Receptors".
Dudley et al., *Molecular Pharmacology,* 1990, 38, 370–377, "Subclass of Angiotensin II Binding Sites and Their Functional . . . ".
Pucell et al., *Endocrinology,* 1991, 128, 1947–1959, "Biochemiical Properties of the Ovarian Granulosa Cell Type 2-Angiotensin II . . . ".
Andrade-Gordon et al., *Biochemical Pharamacology,* 1991, 42, 715–719, "Role of Angiotensin II in the Processes Leading to Ovulation".
Speth et al., *Peptide Research,* 1989, 2, 232–239, "Angiotensin II Receptor Binding and Actions in NG108-15 Cells".
Tallant et tal., *Hypertension,* 1991, 17, 1135–1143, "Identification and Regulation of Angiotensin II Receptor Subtypes on NG108-15 Cells".
*Neuroreport,* vol. 2, No. 6, Jun. 1991, N. M. Barnes et al., pp. 351–353.
*Molecular Pharmacology,* vol. 38, No. 3, Sep. 1990, D. T. Dudley et al., pp. 370–377.
*Brain Research,* vol. 507, No. 2, Jan. 1990, J. M. Barnes, pp. 341–343.
*European Journal of Pharmacology,* vol. 187, No. 1, 2 Oct. 1990, D. R. Gehlert et al., pp. 123–126.
*Biochem. and Biophys. Res. Comm.,* vol. 171, No. 2, 14 Sep. 1990, R. S. L. Chang et al., pp. 813–817.

*Primary Examiner*—Marianne M. Cintins
*Assistant Examiner*—T. J. Criares
*Attorney, Agent, or Firm*—Michael J. Atkins; Charles W. Ashbrook

[57] ABSTRACT

The present invention relates to the use of 4,5,6,7-tetrahydro-1H-imidazo[4,5-c]pyridine-6-carboxylic acids and analogs thereof in antagonizing the binding of angiotensin II to $AT_2$ receptors to treat memory loss.

3 Claims, No Drawings

IMIDAZO-PYRIDINE ANGIOTENSIN II ANTAGONISTS USED TO TREAT MEMORY LOSS

RELATED APPLICATIONS

This is a divisional of U.S. application Ser. No. 07/932,167 filed Aug. 19, 1992, now U.S. Pat. No. 5,338,744, which is a continuation-in-part of U.S. application Ser. No. 07/760,585 filed Sep. 19, 1991, now abandoned, which is a continuation-in-part of U.S. application Ser. No. 07/591,928 filed Oct. 2, 1990, now abandoned.

BACKGROUND OF THE INVENTION

This invention relates to novel utilities for derivatives of 4,5,6,7-tetrahydro-1H-imidazo[4,5-c]pyridine-6-carboxylic acid that have previously been disclosed to be useful for the treatment of hypertension in U.S. Pat. No. 4,812,462 to Blankley et al, issued March 14, 1989. These compounds have the property of antagonizing the binding of angiotensin II (angiotensin II), a peptide hormone, to one subtype of its cellular receptors. In particular, the utility of these compounds arises from activity at the $AT_2$ receptor as described by Bumpus, et al, in *Hypertension*, 1991, 17, 720–721.

The present invention is related to the discovery that the $AT_2$ receptor is found in the central nervous system (CNS) of mammals, and that compounds of general Formula I described herein are effective in blocking angiotensin II binding at $AT_2$ receptors in various brain regions. The present invention is also related to the discovery that alterations in brain biochemistry are observed upon administration of compounds of general Formula I and that these alterations coincide with physiological and behavioral responses.

The present invention is also related to the discovery that $AT_2$ receptors are found in female reproductive organs of mammals including uterus (Data in Table 1, hereof and in Dudley, et al, *Molecular Pharmacol.*, 1990, 38, 370–377) and ovaries (Pucell, et al, *Endocrinology*, 1991, 128, 1947–59). The role of angiotensin II in processes leading to ovulation has been reviewed by Andrade-Gordon, et al, in *Biochemical Pharmacology*, 1991, 42, 715–719. Compounds of general Formula I, inhibit the binding of angiotensin II to $AT_2$ receptors in reproductive tissues, including uterus and ovarian follicles and hence antagonize the effects of angiotensin II therein.

Finally, the present invention is related to the discovery that the $AT_2$ receptor is found in neuronal tumor cells (Speth, et al, *Peptide Research*, 1989, 2, 232–239) and in transformed human neural cells (Tallant, et al, *Hypertension*, 1991, 17, 1135–1143).

SUMMARY OF THE INVENTION

The present invention relates to the use of the compounds of general Formula I which are set forth in Chart I hereof. The present invention embraces the use of pharmaceutically acceptable salts of the compounds of Formula I also.

The compounds of Formula I and pharmaceutically acceptable salts thereof have been found to antagonize the binding of angiotensin II to $AT_2$ receptors. Such a finding renders the compounds useful in treating conditions which are associated with or result from the binding of angiotensin II to $AT_2$ receptors. Thus, compounds of Formula I and pharmaceutically acceptable salts thereof are useful in treating disorders of the CNS which are attributed to the binding of angiotensin II to brain $AT_2$ receptors. The compounds of general Formula I and pharmaceutically acceptable salts thereof are additionally useful in treating conditions of the female reproductive system which result from the binding of angiotensin II to $AT_2$ receptors in reproductive organs. The compounds of general Formula I, radioactive isotopes thereof, and pharmaceutically acceptable salts thereof are also useful as tumor imaging and anticancer agents for brain cancers and other cancers wherein the $AT_2$ receptor is prevalent.

DETAILED DESCRIPTION OF THE INVENTION

Angiotensin II is known to modulate CNS nerve sensitivity to neurotransmitters such as catecholamines, serotonin and enkephalins, and additionally, angiotensin II is a neurotransmitter that regulates the release of hormones from the brain (Phillips, *Ann. Rev. Physiol.*, 1987, 49, 413–35 and Speth, et al, *Research Topics in Physiology*, 1988, 10, 1–34). Agents that block the activity of angiotensin II at $AT_2$ receptors in the CNS will ameliorate disorders associated with abnormal nerve activity and abnormal hormone secretion related to exaggerated $AT_2$ mediated responses to angiotensin II. The compounds of general Formula I, being $AT_2$ antagonists have utility in the treatment and diagnosis of numerous neurological, psychiatric, neuroendocrine, neurodegenerative and neuroimmunological disorders including, but not limited to, those associated with addiction, anxiety, depression, epilepsy, hyperactivity, memory, pain, Parkinsonism, psychosis, regulation of autonomic functions, sleep and tardive dyskinesia.

Barnes, et al, in *Brain Research*, 1990, 507, 341–343, describe the effects of angiotensin II as an inhibitor of potassium stimulated release of ACh from human temporal cortex, giving rise to elevated levels of ACh in cortical tissue. Data from Tables IV, V, and VI hereof show the dose related effect of PD 123319 (Example 1), a compound of general Formula I, in lowering ACh levels in rat striatum and hippocampus. This effect is similar to that described by Usinger, et al, in *Drug Dev. Res.*, 1988, 14, 315–324, wherein rats treated with an angiotensin converting enzyme (ACE) inhibitor, a drug that blocks the formation of angiotensin II, also show reductions in striatal ACh. Usinger relates the ACh reduction in brain tissues to the memory enhancing effects of ACE inhibitors. ACE inhibitors have been shown to enhance cognitive performance in rodent tests of cognition by Costall, et al, in *Pharmacol. Biochem. & Behavior*, 1989, 33, 573–579.

Since both ACE inhibitors and angiotensin receptor antagonists block the ACh accumulating action of angiotensin II in the brain, it is reasonable that both will enhance cognitive performance. Barnes, et al, in *Neuroreport*, 1991, 2, 351–353, have demonstrated that PD 123177 (Example 2), a compound of general Formula I, does indeed possess cognition enhancing actions in rodent behavioral models and that this compound also reverses scopalamine-induced amnesia.

Data from Table IV hereof shows that PD 123319 (Example 1), a compound of general Formula I, matches the ACh lowering ability of haloperidol, a drug used in the treatment of psychotic disorders. It is therefore reasonable that compounds of general Formula I will have utility in the treatment of psychotic disorders.

Another known CNS effect of angiotensin II is stimulation of the release of pituitary and hypothalamic hormones including vasopressin (AVP), oxytocin, adrenocorticotrophic hormone (ACTH), prolactin and luteinizing hormone (LH) (Speth, et al, *Research Topics in Physiology*, 1988, 10, 1–34). Thus, compounds of general Formula I have utility in treatment of various neuroendocrine disorders that are dependant upon the release of hormones resulting from angiotensin II stimulation of $AT_2$ receptors.

Vasopressin (AVP), also known as antidiuretic hormone, is a peptide hormone which causes decreased urinary output, increased urine density and reduced thirst. In normal physiology, it is important for conservation of body fluid (Laszlo, et al, *Pharmacological Rev.*, 1991, 43, 73–108). Schiavone, et al, in *Hypertension*, 1991, 17, 425, describe the effects of $AT_2$ antagonists including PD 123177 (Example 2), a compound of general Formula I, in antagonizing the angiotensin II induced secretion of AVP from isolated rat hypothalamo-neurohypophysial explants. Data in Table VII, hereof, shows the increase in renal free water clearance following administration of Example 1, as a physiological correlate to the blockade of angiotensin II induced AVP secretion. Excessive secretion of AVP has been linked to a number of disorders including excessive water retention associated with the female reproductive disorder known as premenstrual syndrome (PMS) (Janowski, et al, *Psychosomatic Medicine*, 1973, 35, 143–154) and impaired water excretion with adrenal insufficiency (Schrier and Bichet, *J. Lab. Clin. Med.*, 1981, 98, 1–15). It has also been linked to Schwartz-Bartter syndrome (an AVP secreting brain tumor), congestive heart failure, liver cirrhosis, nephrotic syndromes, central nervous injuries, acute psychotic states, lung disease, dysmenorrheic uterine hyperactivity, and premature labor (Lazlo, et al, ibid.). Compounds of general Formula I, by virtue of their ability to block angiotensin II induced AVP secretion, have utility in treatment of the above disorders.

$AT_2$ receptors are known to exist in organs of the female reproductive system. Data shown in Table I, hereof, provides evidence of angiotensin II receptor binding inhibition by compounds of general Formula I in rabbit uterine preparations. According to Dudley, et al, in *Molecular Pharmacology*, 1990, 38, 370–377) this binding inhibition is specific for $AT_2$ (DTT insensitive) receptors. Pucell, et al, in *Endocrinology*, 1991, 128, 1947–59) show $AT_2$ antagonistic properties of PD 123319 (Example 1), a compound of general Formula I, in ovarian cells. More specifically, $AT_2$ receptors are densely located on granulosa cells in atretic follicles of the ovary.

The developmental anatomy and physiology of ovarian follicles is discussed in Guyton's *Textbook of Medical Physiology*, 6th ed., pp 1005–1020 (1981). Follicular granulosa cells are the progenitor of the corpus luteum. They are known to differentiate into the progesterone secreting cells of the corpus luteum upon ovulation. Data provided in Table IX, hereof, show a divergence of $AT_1$ and $AT_2$ receptor populations between corpus lutea ($AT_1$ rich) and granulosa cells from atretic follicles ($AT_2$ rich). Thus, angiotensin receptor subtypes are involved in the regulation of reproductive processes in the ovary including follicle maturation, corpus luteal differentiation, hormonal cycles and follicle atresia.

Table X, hereof, describes the results of autoradiography studies that show the ability of Example 12 to penetrate the ovary and bind specifically to follicles. Compounds of general Formula I, by virtue of their $AT_2$ antagonistic properties and their ability to penetrate ovarian tissues, have utilities associated with the reproductive functions of ovaries including, but not limited to, menstruation, fertility, and disturbances of normal hormonal balances of the estrus cycle.

Table XI, hereof, describes the results of reproductive studies in rats where a representative compound of the present invention, particularly the compound of Example 1, interrupts the menstrual cycle indicating its effectiveness in regulating fertility.

In contrast to the $AT_1$ receptor, which is coupled to G proteins and associated with inositol trisphosphate ($IP_3$) metabolism, the $AT_2$ receptor has been shown to lack G protein coupling and is dissociated from $IP_3$ metabolism (Dudley, et al, *Molecular Pharmacology*, 1990, 38, 370–377). $IP_3$-dissociated angiotensin II receptors have been reported to exist in neuronal tumor cells by Speth, et al, in *Peptide Research*, 1989, 2, 232–239. Additionally, Tallant, et al, in *Hypertension*, 1991, 17, 1135–1143, describe a dramatic upregulation of $AT_2$ receptors when NG108-15 cells, a neurally derived clonal cell line, are induced to differentiate by treatment with dibutyryl cyclic adenosine 3',5'-monophosphate.

Given the numerous effects associated with CNS $AT_2$ receptors already described above, excessive expression of these receptors in neuronal cancers would lead to pathological states. Compounds of general Formula I by virtue of their $AT_2$ antagonizing properties have utility in disrupting the function of tumor cells that contain $AT_2$ receptors. Therefore, they are useful in blocking the actions and/or growth of neuronal tumors as well as other tumors wherein the $AT_2$ receptor is prevalent.

Additionally, radioisotopically labeled compounds of general Formula I have utility as tumor imaging agents and as drugs for tumor-selective irradiation therapy. In both of these utilities, a radioactive atom is attached to a compound of general Formula I which has high affinity for $AT_2$ receptors on the tumor cells. Strategies for tumor imaging agents include the incorporation of $^{125}I$, $^{77}Br$ and $^{18}F$ radiolabels as described in FIG. 1. A compound of general Formula I containing one of these radiolabels carries nonlethal radiation to the $AT_2$ containing tumor where it enables detection of the cancerous site. The synthesis of $^{125}I$-Example 12 is described below. Drugs for tumor-selective irradiation therapy involve incorporation of radioactive isotopes that emit sufficient radioactivity to kill cells such as $^{131}I$ as described in FIG. 2. A compound of general Formula I bearing $^{131}I$ specifically binds to tumors bearing $AT_2$ receptors, resulting in irradiation of the tumor and regression of the cancerous lesion. The synthesis of $^{131}I$-Example 12 is analogous to the synthesis of $^{125}I$-Example 12 described below. Radioisotopically labeled compounds of general Formula I, thus have utility as agents for imaging tumors or as agents that selectively kill tumor cells by irradiation in cancerous states wherein $AT_2$ receptors are prevalent.

The compounds of general Formula I are described and claimed in U.S. Pat. No. 4,812,462 which issued Mar. 14, 1989, which patent is incorporated herein by reference thereto. The compounds of general Formula I and pharmaceutically acceptable salts thereof are described in U.S. Pat. No. 4,812,462 beginning at column 1, line 56 through column 4, line 48. The DETAILED DESCRIPTION OF INVENTION section of U.S.

Pat. No. 4,812,462 describes method of synthesis of the compounds of Formula I (column 10, line 5 through column 17, line 27) and the manner of formulating the compounds, the route of administration and the dosage amount. In practicing the present invention one would use the same dosage amounts, routes of administration and types of pharmaceutical composition as are described in U.S. Pat. No. 4,812,462 (see column 20, line 7 through column 22, line 27).

Receptor Binding Data:

The ability of the incident compounds to displace $^{125}I$- or $^3H$-labeled angiotensin II from cell membrane preparations derived from rabbit uterus and corpus luteum was measured according to the methods described by Dudley, et al, (*Molecular Pharmacology*, 1990, 38, 370–377). Table I shows examples of $IC_{50}$ values for displacement of $^3H$-angiotensin II from rabbit uterus receptor preparations and Table IX compares the relative populations of $AT_1$ and $AT_2$ in ovarian granulosa cells and corpus luteum. Granulosa cells are rich in $AT_2$ receptors as demonstrated by the fact that Example 1 (an $AT_2$ specific agent) displaces nearly all of the 125I-angiotensin II. Conversely, corpus luteum is rich in $AT_1$ receptors as demonstrated by the fact that DUP 753 (an $AT_1$ specific agent) displaces nearly all of the radioligand.

Using the same receptor binding methodology, Table VIII compares the ability of Example 1 (an $AT_2$ specific agent), DUP 753 (an $AT_1$ specific agent) and saralasin (an agent lacking receptor subtype specificity) to displace $^{125}I$-labeled angiotensin II from receptor preparations derived from various segments of rat brain. The concentration of all three antagonist compounds in these experiments is 1 $\mu M$ (above the maximal effect concentration). Both Example 1 and Dup 753 displace a fraction of the $^{125}I$-angiotensin II that is displaced by saralasin (Sat), indicating the presence of both receptor subtypes in each area of brain examined.

Table II shows examples or $IC_{50}$ values for the incident compounds in whole rat brain. Since receptor-specific binding in whole brain is low and is a mixture of two subtypes, an alternative protocol (Bennett and Snyder, *Eur. J. Pharmacol.*, 67, 11–25) was used. This method includes DTT and thereby eliminates binding at $AT_1$ receptors, thus-allowing evaluation of $AT_2$ receptor events. The whole brain assay suffers from a low specific to nonspecific binding ratio relative to assays run in other tissues but it is possible to demonstrate the inhibitory action of compounds of general Formula I on the binding of angiotensin II to $AT_2$ receptors. In summary, the above receptor binding data show that these compounds interact with $AT_2$ receptors in both brain and reproductive tissues.

Autoradiography:

$^{125}I$-Labeled Example 12 was prepared from Example 13 according to the following procedure: A solution of Example 13 (2.0 $\mu g$, 4.1 nMol) in methanol (2 $\mu L$), was treated with a solution of $Na^{125}I$ (5.0 mCi, 2.3 nMol) in potassium phosphate buffer (0.5 M, pH 7.2, 40 $\mu L$). The iodination was initiated by addition of chloramine-T (30 $\mu g$, 132 nMol) that was diluted to a concentration of 0.05 M in the same buffer as above. After shaking at room temperature for one minute the reaction was quenched with sodium metabisulfite (10 mg). HPLC purification of the reaction mixture on an Altech RPC $C_{18}$ reversed phase column with an isocratic mobile phase of acetonitrile (30%) and 0.1% aqueous trifluoroacetic acid (70%) afforded pure $^{125}I$-Example 12 as its trifluoroacetate salt upon evaporation of solvents. This labeled material was reconstituted in 5% aqueous dextrose containing 30 mg/mL of the disodium salt of unlabeled Example 12 and adjusted to pH 9 by addition of several $\mu L$ of 1 mM NaOH.

Male and female Sprague-Dawley rats (Charles River, Wilmington, average weight 281 g) were used in the autoradiography studies. Animals were on a fixed light cycle with unrestricted access to normal rat chow and water prior to the experiment. Rats received 30 mg/kg $^{125}I$-labeled Example 12 (966 $\mu Ci$/kg), injected via the tail vein over one minute. Animals were killed at 15 or 60 minutes postdose by halothane anesthesia and were rapidly frozen in acetone with dry ice. Carcasses were subsequently embedded in methylcellulose ice for whole-body sectioning and autoradiography. Autoradiograms were analyzed by computer assisted densitometry.

Results of the autoradiographical experiments are summarized in Table X. A relative scale of radioactivity is assigned with background equal to 0 and the most dense reading (liver and intestines) equal to 10. The sites that are highly labeled by $^{125}I$-Example 12 include liver, intestines and bladder which are all indicative of excretory processes since these tissues show negligible $AT_2$ receptors in binding experiments. Another site that is highly labeled is the ovarian follicle. It is the most highly labeled non-excretory organ. All other tissues show weaker radioactivity. These results demonstrate the ability of Example 12 to selectively distribute to the ovarian follicle, a female reproductive organ.

Effects of Example 1 on Estrous Cycles in the Mature Rat

Female rats underwent vaginal smearing every morning for 5 weeks; rats with regular 4-day cycles (proestrus, estrus, metestrus, diestrus) were chosen for further study. Groups of rats (n=5) were implanted with Alzet osmotic minipumps (Model 2ML2) containing Example 1 or vehicle on the afternoon of estrus (approximately 2 PM). Drug-treated animals received 30 mg/kg/day Example I for 14 days. Cycles were continually monitored throughout the treatment period and for an additional 20 to 22 days posttreatment.

Data are presented in Table XI. Vehicle-treated animals continued to cycle in a 4-day pattern throughout the study. Example 1-treated rats were acyclic during the 14-day treatment interval but resumed cycling during the posttreatment observation period.

Effects of Example 1 on Brain ACh Levels

Example 1 was given by IP administration to normal rats at 1,10, 30 and 60 mg/kg. Thirty minutes after dosing, the rats were sacrificed by exposure to microwave irradiation. ACh levels in striatum and hippocampus were then measured by HPLC assay with electrochemical detection according to the method of Beley, et al, (*J. Liquid Chrom.*, 1987, 10, 2977) using the ACh analysis system from Bioanalytical Systems, Inc. Table IV shows the dose responsive nature of ACh reduction following treatment with Example 1. Haloperidol (2 mg/kg, IP) provides a positive control. DUP 753 (an $AT_1$ specific antagonist of angiotensin II) shows no effect at 30 mg/kg, IP. Example I matched the efficacy of haloperidol, a known antipsychotic drug, in lowering striatal ACh. Table V shows a comparable lowering of ACh levels in the hippocampus and striatum by Example 1 at a dose of 30 mg/kg. Table VI shows the time course of the ACh lowering action of Example 1. Peak effect is at 0.5 hours, with ACh levels gradually returning to control levels in 24 hours.

The data in Tables IV, V and VI indicate that Example I, a compound of general Formula I, inhibits the normal role of angiotensin II in brain tissues. Normally, angiotensin II inhibits release of ACh from brain tissues thereby elevating ACh levels in brain tissues. Example I, an $AT_2$ specific agent lowers ACh content in brain tissues in a dose dependant and time dependant manner. These data provide evidence in support of the use of compound of general Formula I in treatment of conditions wherein the CNS responsiveness to angiotensin II is abnormal and leads to inappropriate elevation of brain ACh content, including, but not limited to, the treatment of memory disorders and psychoses.

Effects of Example 1 on Renal Free Water Clearance

Dogs were anesthetized with sodium pentobarbital after an overnight fast. Animals were placed on a pre-warmed surgical table, intubated and prepared for renal clearance experiments. Femoral arteries were cannulated for aortic blood pressure measurements and for blood sampling. A femoral vein was cannulated and used for the infusion of inulin. A left flank incision was made to expose the kidney and ureter. An electromagnetic flow probe was placed on the left renal artery and the left ureter was cannulated for urine collection. An intrarenal infusion of 5% dextrose in water (D5W, 50 $\mu$L/min) was administered throughout the protocol except during drug treatment intervals. A priming dose of 50 mL D5W containing 200 mg/kg insulin was administered to each dog via the femoral vein catheter and then followed by a sustained infusion of inulin in D5W (15 mg/mL, 0.075 mL/min/kg).

Following a 45 minute equilibration period, a series of ten 15-minute renal clearance periods were obtained. A clearance consisted of a timed urine collection with a midpoint blood sample. The first two 15-minute clearances, during which vehicle was infused, were designated as predose. Separated groups of animals received vehicle (control) or Example 1 in three cumulative doses (3, 30 and 300 $\mu$g/kg/min, n=5). Each dose was infused intrarenally over 35 minutes, the animals were allowed to stabilize for 5 minutes, and two 15-minute clearances were collected. After the final dose, D5W was infused for a 60 minute washout and during two 15-minute clearances. These last two clearances were designated as postdose.

Plasma and urinary electrolytes were determined with an ion selective electrode analyzer. Urine and plasma inulin concentrations were assayed using an anthrone colorimetric method (Davidson, et al, *J. Lab and Clin. Med.*, 1963, 62, 351–356). Renal clearances and fractional excretion were calculated using standard formulas (Vander, *Renal Physiology*, 4th ed, pp 44–52 (1991)). Table VII shows the free water clearance data for animals of the vehicle control group and of the Example 1 treated group. The vehicle control animals show a slight but statistically insignificant reduction in free water clearance as the experiment progressed. The Example 1 treated animals show an increase in free water clearance that is dose dependant and statistically significant when compared to the vehicle control. Free water clearance is increased by up to 370% from pre-dose levels upon treatment with Example 1. These data provide evidence in support of the use as a treatment for conditions wherein excessive responsiveness to angiotensin II at $AT_2$ receptors results in inappropriate water retention, including, but not limited to, neurohormonal conditions related to excessive vasopressin secretion such as premenstrual syndrome, impaired water excretion with adrenal insufficiency and Schwartz-Bartter syndrome.

TABLE I

IC$_{50}$ Values in Rabbit Uterine Preparations

| Ex | R$_1$ | R$_5$ | IC$_{50}$ (M) |
|---|---|---|---|
| 1 | 3-Me-4-NMe$_2$—PhCH$_2$ | COCHPh$_2$ | $2.1 \times 10^{-8}$ |
| 2 | 3-Me=4-NH$_2$—PhCH$_2$ | COCHPh$_2$ | $3.2 \times 10^{-8}$ |
| 3 | 3-Me-4-MeO—PhCH$_2$ | COCHPh$_2$ | $2.6 \times 10^{-8}$ |
| 4 | 1-Adamantylethyl | COCHPh$_2$ | $9.1 \times 10^{-8}$ |
| 5 | 3-Me-4-NMe$_2$—PhCH$_2$ | COCH(4-F—Ph)$_2$ | $3.8 \times 10^{-8}$ |
| 6 | 3-Me-4-MeO—PhCH$_2$ | CO(9-Fluorenyl) | $1.2 \times 10^{-6}$ |
| 7 | 3-Me-4-NO$_2$—PhCH$_2$ | COCHPh$_2$ | $6.7 \times 10^{-8}$ |
| 8 | PhCH$_2$ | COCHPh$_2$ | $7.4 \times 10^{-8}$ |
| 9 | 3-Me-4-MeO—PhCH$_2$ | COCH$_2$Ph | $9.5 \times 10^{-8}$ |
| 10 | 3-Me-4-MeO—PhCH$_2$ | COCH(4-Cl—Ph)$_2$ | $1.2 \times 10^{-7}$ |
| 11 | 3-Me-4-MeCONH—PhCH$_2$ | COCHPh$_2$ | $1.5 \times 10^{-7}$ |
| 12 | 3-I-4-HO-5-Me—PhCH$_2$ | COCHPh$_2$ | $2.5 \times 10^{-8}$ |

TABLE II

IC$_{50}$ Values in whole Rat Brain Preparations

| Example | R$^1$ | IC$_{50}$ (M) |
|---|---|---|
| 1 | 3-Me-4-Me$_2$N—PhCH$_2$ | $2.0 \times 10^{-7}$ |
| 4 | i-Adamantylethyl | $1.8 \times 10^{-7}$ |
| 12 | 3-Me-4-NH$_2$—PhCH$_2$ | $5.7 \times 10^{-7}$ |
| 15 | 4-CF$_3$—PhCH$_2$ | $7.8 \times 10^{-7}$ |
| 16 | 3-Me—PhCH$_2$ | $1.6 \times 10^{-6}$ |
| 8 | PhCH$_2$ | $3.8 \times 10^{-6}$ |

TABLE III

Compound Names

| Example | Name |
|---|---|
| 1 | (S)-(—)-1-[[4-dimethylamino)-3-methylphenyl]methyl]-5-(diphenylacetyl)-4,5,6,7-tetrahydro-1H-imidazo[4,5-c]-pyridine-6-carboxylic acid |
| 2 | (S)-(—)-1-[(4-amino-3-methylphenyl)-methyl]-5-(diphenylacetyl)-4,5,6,7-tetrahydro-1H-imidazo[4,5-c]pyridine-6-carboxylic acid |
| 3 | (S)-(—)-5-(diphenylacetyl)-4,5,6,7-tetrahydro-1-[(4-methoxy-3-methyl-phenyl)methyl]-1H-imidazo[4,5-c]pyridine-6-carboxylic acid |
| 4 | (S)-(—)-5-(diphenylacetyl)-4,5,6,7-tetrahydro-1-(2-tricyclo[3.3.1.1$^{3,7}$]dec-1-ylethyl-1H-imidazo[4,5-c]pyridine-6-carboxylic acid |
| 5 | (S)-(—)-5-[bis(4-fluorophenyl)acetyl]-1-[[4-(dimethylamino)-3-methyl-phenyl]methyl]-4,5,6,7-tetrahydro-1H-imidazo[4,5-c]pyridine-6-carboxylic acid |
| 6 | (S)-(—)-5-(9H)-fluoren-9-ylcarbonyl)-4,5,6,7-tetrahydro-1-[(4-methoxy-3-methylphenyl)methyl]-IH-imidazo-[4,5-c]pyridine-6-carboxylic acid |
| 7 | (S)-(—)-5-(diphenylacetyl)-4,5,6,7- |

TABLE III-continued

Compound Names

| Example | Name |
|---------|------|
|  | tetrahydro-1-[(3-methyl-4-nitrophenyl)-methyl]-4-nitrophenyl)methyl]-1H-imidazo[4,5-c]pyridine-6-carboxylic acid |
| 8 | (S)-(−)-5-(diphenylacetyl)-4,5,6,7-tetrahydro-1-(phenylmethyl)-1H-imidazo[4,5-c]pyridine-6-carboxylic acid |
| 9 | (S)-(−)-4,5,6,7-tetrahydro-1-[(4-methoxy-3-methylphenyl)methyl]-5-(phenylacetyl)-1H-imidazo-[4,5-c]pyridine-6-carboxylic acid |
| 10 | (S)-(−)-5-[bis(4-chlorophenyl)acetyl]-4,5,6,7-tetrahydro-1-[(4-methoxy-3-methylphenyl)methyl]-1H-imidazo-[4,5-c]pyridine-6-carboxylic acid |
| 11 | (S)-(−)-[[4-(acetylamino)-3-methylphenyl]methyl]-5-(diphenylacetyl)-4,5,6,7-tetrahydro-1H-imidazo-[4,5-c]pyridine-6-carboxylic acid |
| 12 | (S)-(−)-5-(diphenylacetyl)-1-[(4-hydroxy-3-iodo-5-methylphenyl)methyl]-4,5,6,7-tetrahydro-1H-imidazo[4,5-c]pyridine-6-carboxylic acid |
| 13 | (S)-(−)-5-(diphenylacetyl)-1-[(4-hydroxy-3-methylphenyl)methyl]-4,5,6,7-tetrahydro-1H-imidazo[4,5-c]pyridine-6-carboxylic acid |
| 14 | (S)-(−)-1-[(4-aminophenyl)-methyl]-5-(diphenylacetyl)-4,5,6,7-tetrahydro-1H-imidazo-[4,5-c]pyridine-6-carboxylic acid |
| 15 | (S)-(−)-5-(diphenylacetyl)-4,5,6,7-tetrahydro-1-[[4-(trifluoromethyl)-phenyl]methyl]-1H-imidazo[4,5-c]pyridine-6-carboxylic acid |
| 16 | (S)-(−)-5-(diphenylacetyl)-4,5,6,7-tetrahydro-1-[(3-methylphenyl)methyl]-1H-imidazo[4,5-c]pyridine-6-carboxylic acid |

TABLE IV

Effect of Example 1 on Rat Striatal Acetylcholine (ACh) Concentrations

| Treatment | Dose (mg/kg, IP) | ACh (nM/g ± SEM) |
|-----------|------------------|------------------|
| Vehicle (Control) | — | 61.0 ± 2.33 |
| Example 1 | 1 | 57.9 ± 1.86 |
| " | 10 | 48.1 ± 0.99* |
| " | 30 | 37.6 ± 2.10* |
| " | 60 | 41.1 ± 1.89* |
| Haloperidol | 2 | 36.9 ± 3.27* |
| DUP 753 | 30 | 67.5 ± 5.71 |

Rats were administered test compounds 0.5 hours before animals were sacrificed. ACh concentrations were determined as described below. Each value is a mean of at least 4 animals. Results were analyzed by a one-way analysis of variance followed with Newman-Keuls multiple comparison test.
*Level of significance is $p < 0.05$.

TABLE V

Effect of Example 1 on Concentrations of ACh in Rat Striatum and Hippocampus

| | ACh (nM/g ± SEM) | |
|---|---|---|
| Treatment | Striatum | Hippocampus |
| Vehicle (Control) | 52.9 ± 1.72 | 23.9 ± 2.39 |
| Example 1 | 39.7 ± 0.99* | 15.1 ± 1.55* |

Animals were treated IP with 30 mg/kg of Example 1. At 0.5 hours post dosing ACh concentrations were determined as described below.
*Statistical treatment of data is as described in Table IV.

TABLE VI

Time Course of Effect of Example 1 (10 mg/kg, IP) on Ach Concentration in Rat Striatum

| Treatment | Time (h) | ACh (nM/g ± SEM) |
|-----------|----------|------------------|
| Control | — | 65.4 ± 2.47* |
| Example 1 | 0.5 | 37.6 ± 2.10* |
| " | 1.0 | 47.9 ± 2.24* |
| " | 3.0 | 50.2 ± 4.53* |
| " | 6.0 | 55.8 ± 4.28 |
| " | 24.0 | 61.3 ± 2.30 |

Rats were administered Example 1 and sacrificed at the indicated times. ACh concentrations were determined as described below.
*Statistical treatment of data is as described in Table IV.

TABLE VII

Effect of Example 1 on Renal Free Water Clearance

| | | Free Water Clearance | |
|---|---|---|---|
| Time (min) | Vehicle Control | mL/min | Change from Predose |
| 30 | (predose) | −0.19 ± 0.06 | — |
| 60 | — | −0.22 ± 0.06 | −16% |
| 90 | — | −0.26 ± 0.05 | −37% |
| 120 | — | −0.29 ± 0.05 | −53% |
| 150 | (postdose) | −0.27 ± 0.06 | |

| | | Free Water Clearance | |
|---|---|---|---|
| Time (min) | Example 1 Dose (Kg/kg/min) | mL/min | Change from Predose |
| 30 | 0 (predose) | −0.24 ± 0.05 | — |
| 60 | 3 | −0.11 ± 0.13 | +54% |
| 90 | 30 | +0.11 ± 0.19* | +150% |
| 120 | 300 | +0.64 ± 0.30** | +370% |
| 150 | 0 (postdose) | +0.29 ± 0.10*** | |

Data are group means ± standard error. Significant difference from vehicle control group.
*$p = 0.097$
**$p = 0.015$
***$p = 0.002$

TABLE VIII

Activity of Angiotensin II Antagonists (10 μM) by Brain Region

| | $^{125}$I-Angiotensin II Bound (cpm) | | | |
|---|---|---|---|---|
| Tissue (Rat) | Total | +SAR | +Example 1 | +DUP 753 |
| Cortex | 766 | 336 | 507 | 554 |
| Cerebellum | 571 | 269 | 446 | 346 |
| Striatal Membrane | 2462 | 1295 | 1838 | 2067 |
| Brain Stem | 2124 | 288 | 1258 | 787 |
| Cortical Neurons | 2647 | 293 | 2118 | 384 |

TABLE IX $^{125}$I-Angiotensin II Binding: Inhibition by Subtype Specific Receptor Antagonists

| | % Inhibition with 1 μM Antagonist | |
|---|---|---|
| Tissue | DUP 753 (AT$_1$ Blocker) | PD 123319 (Example 1) (AT$_2$ Blocker) |
| Granulosa cell* | 3% | 97% |
| Corpus luteum** | 97% | 3% |

*Adapted from Pucell, et al, Endocrinology, 1991, 128, 1947-59.
**Data from Warner-Lambert Co., Ann Arbor, MI.

TABLE X

Anatomical Distribution of $^{125}$CI-Example 12 by Whole Body Autoradiography in Rats

| Location | Relative Radioactivity |
|----------|------------------------|
| Background | 0 |

TABLE X-continued

Anatomical Distribution of $^{125}$CI-Example 12 by Whole Body Autoradiography in Rats

| Location | Relative Radioactivity |
|---|---|
| Testicle | 1–2 |
| Uterus | 2–3 |
| Thymus | 3 |
| Adrenal | 3 |
| Heart | 3 |
| Blood | 4 |
| Lung | 4 |
| Bladder* | 4–6 |
| Kidney | 4–8 |
| Salivary gland | 6–7 |
| Ovary (non-follicular) | 3–5 |
| Ovarian follicle | 9 |
| Liver* | 10 |
| Intestines* | 10 |

*Represents excretion processes since receptor binding assays show no AT$_2$ receptor in these tissues.

TABLE XI

Effects of Example 1 on Cyclicity in Female Rats

|  | Pre Rx | Rx | Post Rx |
|---|---|---|---|
| Vehicle |  |  |  |
| Length of cycles (days) | 4 | 4.5 | 4 |
| Number of cycles observed | 10 | 3 | 5 |
| Example 1 |  |  |  |
| Length of cycles (days) | 4 | 14.4 | 3.9 |
| Number of cycles observed | 10 | 1 | 4 |

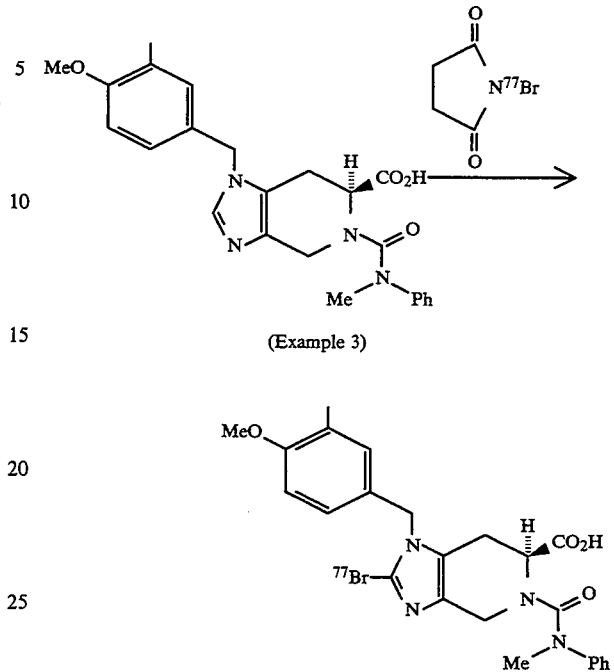

(Example 3)

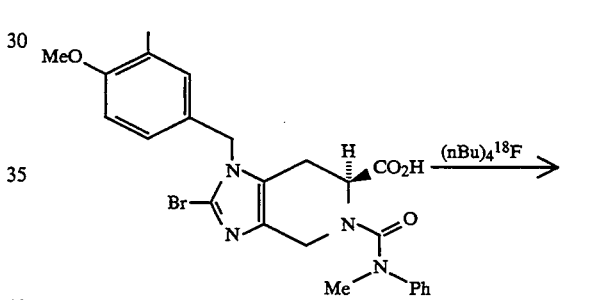

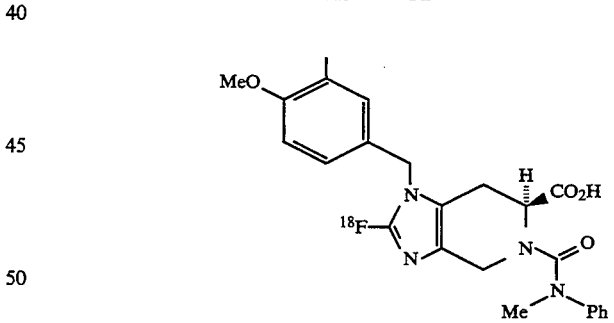

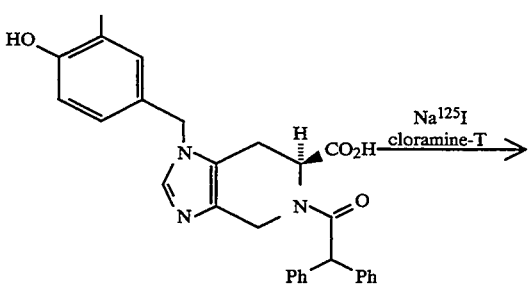

(Example 13)

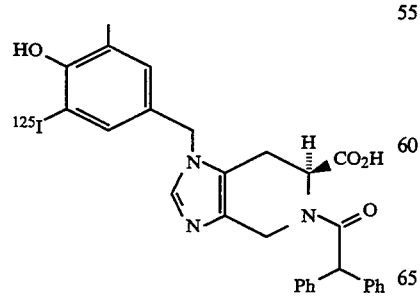

($^{125}$I-Example 12)

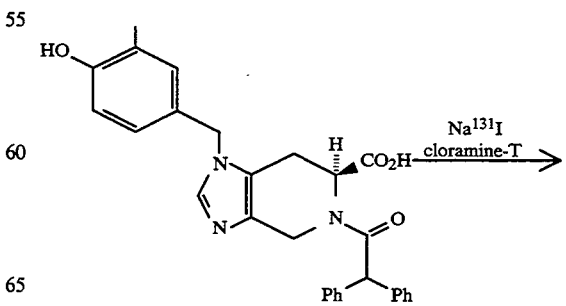

(Example 13)

-continued

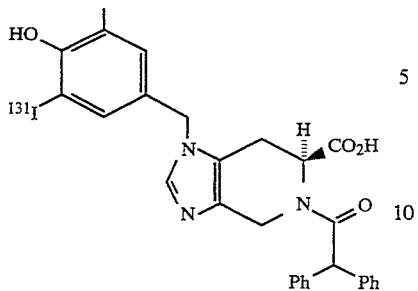

($^{131}$I-Example 12)

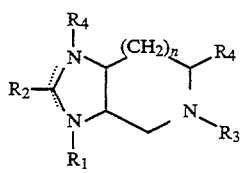

wherein
(1) — is a single or a double bond;
(2) one of $R_1$ is present and is
   (a) alkyl of from four to twenty carbons, inclusive,
   (b)

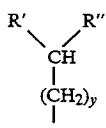

wherein y is zero, one, two, three, four, or five, R' is cycloalkyl of from four to twenty carbons, inclusive in a one-, two-, or three-saturated ring system, said ring consisting of from four to eight carbons inclusive, each ring unsubstituted or substituted by a straight or branched lower alkyl group, naphthyl, heteroaryl consisting of 2-, 3-, or 4-pyridyl; 1-, 2-, or 4-imidazolyl; 1-, 2-, 3-, 4-, 5-, 6-, or 7-indolyl; 2-, or 3-thienyl; 2-, or 3-furyl; or 1-, 2-, or 3-pyrazolyl, phenyl unsubstituted or substituted with of from one through five substituents selected from the group consisting of lower alkyl, halo, trifluoromethyl, hydroxy, lower alkoxy, lower alkyl acyloxy, amino, N-lower monoalkylamino, N,N-lower dialkylamino, lower thioalkyl, lower alkylsulfonyl, nitro and

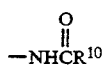

wherein $R^{10}$ is lower alkyl, phenyl unsubstituted or substituted by lower alkyl, or —$NHR_{11}$ wherein $R_{11}$ is hydrogen or lower alkyl, and R'' is hydrogen, lower alkyl, cycloalkyl of from four to twenty carbons, inclusive in a one-, two-, or three-saturated ring system, said ring consisting of from four to eight carbons inclusive, each ring unsubstituted or substituted by a straight or branched lower alkyl group, naphthyl, phenyl unsubstituted or substituted with of from one through five substituents selected from the group consisting of alkyl, halo, trifluoromethyl, amino, N-lower monoalkylamino, N, N-lower dialkylamino, lower thioalkyl, lower alkylsulfonyl, and nitro;

(3) $R_2$ is
   (a) hydrogen,
   (b) halo,
   (c) lower alkyl,
   (d) R'—$(CH_2)_x$ wherein x is one, two, three, four, or five and R' is independently as defined above,
   (e)

wherein R' is independently as defined above, or
   (f) R'—CH(OH)— wherein R' is independently as defined above;

(4) $R_3$ is
   (a) R'—(—CH—)$_x$ wherein x and R' are independently as defined above,
   (b)

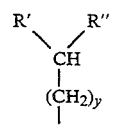

wherein R' and y are independently as defined above, and R''' is lower alkyl, cycloalkyl of from four to twenty carbons, inclusive in a one-, two-, or three-saturated ring system, said ring consisting of from four to eight carbons inclusive, each ring unsubstituted or substituted by a straight or branched lower alkyl group, naphthyl, phenyl unsubstituted or substituted with of from one to five substituents selected from the group consisting of alkyl, halo, trifluoromethyl, amino, N-lower monoalkylamino, N,N-lower dialkylamino, lower thioalkyl, lower alkylsulfonyl, and nitro;

wherein $R_5$ is
   (i) alkyl of from one to fifteen carbons, inclusive,
   (ii)

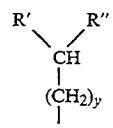

wherein R', R'', and y are independently as defined above,
   (iv) —(—CH=$CR_6$—)—$R_1$ wherein $R_6$ is hydrogen or lower alkyl and $R_1$ is as defined above,
   (v)

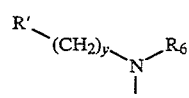

wherein y, R', and $R_6$ are independently as defined above, (vi) R'—(—CH$_2$—)$_y$—O— wherein y and R' are independently as defined above, (vii)

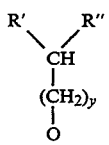

wherein R', R" and y are independently as defined above, (d)

wherein R$_5$ is independently as defined above;

(5) R$_4$ is
(a) —CH$_2$OR$_7$ wherein R$_7$ is hydrogen, lower acyl, a lower alkyl,
(b)

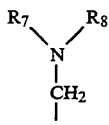

wherein R$_7$ is independently as defined above and R$_8$ is hydrogen, lower alkyl, or benzyl, (c)

(d) —C≡N,
(e)

wherein R$_9$ is hydrogen, lower alkyl, or benzyl; and
(6) n is one; with the overall proviso that R$_9$ cannot be hydrogen, methyl, or ethyl when R$_3$ is R'—(CH$_2$)$_x$ or

wherein R$_5$ is R'—(CH$_2$)$_y$O— or

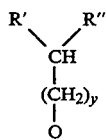

wherein each of R', R", x, and y are as defined above.

We claim:

1. A method for treating memory disorder in a patient in need of treatment comprising administering an effective amount of a compound of Formula I

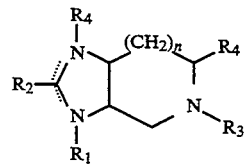

wherein
(1)—is a single or a double bond;
(2) one of R$_1$ is present and is
(a) alkyl of from four to twenty carbons, inclusive,
(b)

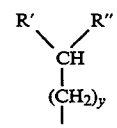

wherein y is zero, one, two, three, four, or five, R' is cycloalkyl of from four to twenty carbons, inclusive in a one-, two-, or three-saturated ring system, said ring consisting of from four to eight carbons inclusive, each ring unsubstituted or substituted by a straight or branched lower alkyl group, naphthyl, heteroaryl consisting of 2-, 3-, or 4-pyridyl; 1-, 2-, or 4-imidazolyl; 1-, 2-, 3-, 4-, 5-, 6-, or 7-indolyl; 2-, or 3-thienyl; 2-, or 3-furyl; or 1-, 2-, or 3-pyrazolyl, phenyl unsubstituted or substituted with of from one through five substituents selected from the group consisting of lower alkyl, halo, trifluoromethyl, hydroxy, lower alkoxy, lower alkyl acyloxy, amino, N-lower monoalkylamino, N, N-lower dialkylamino, lower thioalkyl, lower alkylsulfonyl, nitro and

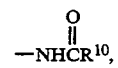

wherein R$^{10}$ is lower alkyl, phenyl unsubstituted or substituted by lower alkyl, or —NHR$_{11}$ wherein R$_{11}$ is hydrogen or lower alkyl, and R" is hydrogen, lower alkyl, cycloalkyl of from four to twenty carbons, inclusive in a one-, two-, or three-saturated ring system, said ring consisting of from four to eight carbons inclusive, each ring unsubstituted or substituted by a straight or branched lower alkyl group, naphthyl, phenyl unsubstituted or substituted with of from one through five substituents selected from the group consisting of alkyl, halo, trifluoromethyl, amino, N-lower monoalkylamino, N, N-lower dialkylamino, lower thioalkyl, lower alkylsulfonyl, and nitro;

(3) R$_2$ is
(a) hydrogen,
(b) halo,
(c) lower alkyl,
(d) R'—(CH$_2$)$_x$ wherein x is one, two, three, four, or five and R' is independently as defined above,
(e)

wherein R' is independently as defined above, or (f) R'—CH(OH)— wherein R' is independently as defined above;

(4) R₃ is (a) R'—(—CH—)ₓ wherein x and R' are independently as defined above, (b)

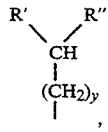

wherein R' and y are independently as defined above, and R''' is lower alkyl, cycloalkyl of from four to twenty carbons, inclusive in a one-, two-, or three-saturated ring system, said ring consisting of from four to eight carbons inclusive, each ring unsubstituted or substituted by a straight or branched lower alkyl group, naphthyl, phenyl unsubstituted or substituted with of from one to five substituents selected from the group consisting of alkyl, halo, trifluoromethyl, amino, N-lower monoalkylamino, N,N-lower dialkylamino, lower thioalkyl, lower alkylsulfonyl, and nitro;

wherein R₅ is (i) alkyl of from one to fifteen carbons, inclusive, (ii)

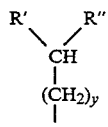

wherein R', R'', and y are independently as defined above, (iv) —(—CH=CR₆—)—R₁ wherein R₆ is hydrogen or lower alkyl and R₁ is as defined above, (v)

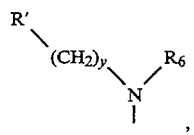

wherein y, R', and R₆ are independently as defined above, (vi) R'—(—CH₂—)ᵧ—O— wherein y and R' are independently as defined above, (vii)

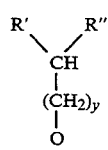

wherein R', R'', and y are independently as defined above,

wherein R₅ is independently as defined above;

(5) R₄ is (a) —CH₂OR₇ wherein R₇ is hydrogen, lower acyl, a lower alkyl, (b)

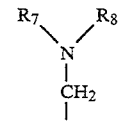

wherein R₇ is independently as defined above and R₈ is hydrogen, lower alkyl, or benzyl, (c)

(d) —C≡N, (e)

wherein R₉ is hydrogen, lower alkyl, or benzyl; and (6) n is one; with the overall proviso that R₉ cannot be hydrogen, methyl, or ethyl when R₃ is R'—(CH₂)ₓ or $$-\overset{O}{\underset{\|}{C}}-R_5$$

wherein R₅ is R'—(CH₂)₆O— or

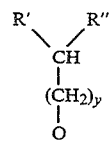

wherein each of R', R'', x, and y are as defined above.

2. The method of claim 1 wherein the compound is:
(S)-(—)-1-[[4-dimethylamino)-3-methylphenyl]methyl]-5-(diphenylacetyl)-4,5,6,7-tetrahydro-1H-imidazo[4,5-c]-pyridine-6-carboxylic acid,
(S)-(—)-1-[(4-amino-3-methylphenyl)methyl]-5-(diphenylacetyl)-4,5,6,7-tetrahydro-1H-imidazo[4,5-c]pyridine-6-carboxylic acid,
(S)-(—)-5-(diphenylacetyl)-4,5,6,7-tetrahydro-1-[(4-methoxy-3-methyl-phenyl)methyl]-1H-imidazo[4,5-c]pyridine-6-carboxylic acid,
(S)-(—)-5-(diphenylacetyl)-4,5,6,7-tetrahydro-1-(2-tricyclo[3.3.1.1³,⁷]dec-1-ylethyl-1H-imidazo[4,5-c]pyridine-6-carboxylic acid,
(S)-(—)-5-[bis (4-fluorophenyl)acetyl]-1-[[4-(dimethylamino)-3-methyl-phenyl]methyl]-4,5,6,7-tetrahydro-1H-imidazo[4,5-c]pyridine-6-carboxylic acid, (S)-(—)-5-(9H)-fluoren-9-ylcarbonyl)-4,5,6,7-tetrahydro-1-[(4-methoxy-3-methylphenyl)methyl]-1H-imidazo-[4,5-c]pyridine-6-carboxylic acid, (S)-(—)-5-(diphenylacetyl)-4,5,6,7-tetrahydro-1-[(3-methyl-4-nitrophenyl)-methyl]-4-nitrophenyl)methyl]-1H-imidazo[4,5-c]pyridine-6-carboxylic acid, (S)-(—)-5-(diphenylacetyl)-4,5,6,7-tetrahydro-1-(phenylmethyl)-1H-imidazo[4,5-c]pyridine-6-carboxylic acid, (S)-(—)-4,5,6,7-tetrahydro-1-[(4-methoxy-3-methylphenyl)methyl]-5-(phenylacetyl)-1H-imidazo-[4,5-c]pyridine-6-carboxylic acid, (S)-(—)-5-[bis(4-chlorophenyl)acetyl]-4,5,6,7-tetrahydro-1-[(4-methoxy-3-methylphenyl)methyl]-1H-imidazo-[4,5-c]pyridine-6-carboxylic acid, (S)-(—)-[[4-(acetylamino)-3-methylphenyl]methyl]-5-(diphenylacetyl)-4,5,6,7-tetrahydro-1H-imidazo-[4,5-c]pyridine-6-carboxylic acid, (S)-(—)-5-(diphenylacetyl)-1-[(4-hydroxy-3-iodo-5-methylphenyl)methyl]-4,5,6,7-tetrahydro-1H-imidazo[4,5-c]pyridine-6-carboxylic acid, (S)-(—)-5-(diphenylacetyl)-1-[(4-hydroxy-3-methylphenyl)methyl]-4,5,6,7-tetrahydro-1H-imidazo-[4,5-c]pyridine-6-carboxylic acid, (S)-(—)-1-[(4-aminophenyl)-methyl]-5-(diphenylacetyl)-4,5,6,7-tetrahydro-1H-imidazo[4,5-c]pyridine-6-carboxylic acid, (S)-(—)-5-(diphenylacetyl)-4,5,6,7-tetrahydro-1-[[4-(trifluoromethyl)phenyl]methyl]-1H-imidazo[4,5-c]pyridine-6-carboxylic acid, and (S)-(—)-5-(diphenylacetyl)-4,5,6,7-tetrahydro-1-[(3-methylphenyl)methyl]-1H-imidazo-[4,5-c]pyridine-6-carboxylic acid.

3. The method of claim 2, wherein the compound is (S)-(—)-1-[[4-dimethylamino)-3-methylphenyl]methyl]-5-diphenylacetyl)-4,5,6,7-tetrahydro-1H-imidazo[4,5-c]-pyridine-6-carboxylic acid.

* * * * *

UNITED STATES PATENT AND TRADEMARK OFFICE
CERTIFICATE OF CORRECTION

PATENT NO. : 5,444,069
DATED     : August 22, 1995
INVENTOR(S) : Dudley, et. al.

It is certified that error appears in the above-indentified patent and that said Letters Patent is hereby corrected as shown below:

Title page, under item [22] after "Filed: Apr. 13, 1994" the following should have been inserted--Related U.S. Application Data item [63] Divisional of Ser. No. 07/932,167, filed August 19, 1992, now Patent No. 5,338,774, which is a Continuation-in-Part of U.S. Application Ser. No. 07/760,585, filed Sep. 19, 1991, now abandoned, which is a Continuation-in- Part of Ser. No. 07/591,928, filed Oct. 2, 1990, now abandoned.--

Column 18, line 42, delete subscript " 6 " and insert instead subscript " y ".

Signed and Sealed this

Thirtieth Day of July, 1996

Attest:

BRUCE LEHMAN

Attesting Officer         Commissioner of Patents and Trademarks